United States Patent [19]
Kawashima et al.

[11] Patent Number: 5,458,873
[45] Date of Patent: Oct. 17, 1995

[54] CARBOXYVINYL POLYMER HAVING NEWTONIAN VISCOSITY

[75] Inventors: Yoichi Kawashima, Kyoto; Mitsuaki Kuwano, Toyonaka, both of Japan

[73] Assignee: Santen Pharmaceutical Co., Ltd., Osaka, Japan

[21] Appl. No.: 986,284

[22] Filed: Dec. 7, 1992

[30] Foreign Application Priority Data

Dec. 13, 1991 [JP] Japan ................... 3-330910

[51] Int. Cl.$^6$ .................. A61K 47/32; C08J 3/28
[52] U.S. Cl. .................. 424/78.04; 424/78.31; 514/915; 522/86; 522/153; 523/318; 523/300
[58] Field of Search ............. 424/78.31, 78.04; 574/772.6, 784, 915; 522/86, 153; 528/502; 523/318, 300

[56] References Cited

U.S. PATENT DOCUMENTS

| | | |
|---|---|---|
| 3,649,358 | 3/1972 | Johnston, II . |
| 3,884,826 | 5/1975 | Phares, Jr. et al. ............ 424/78.04 |
| 3,949,116 | 4/1976 | Lawson et al. . |
| 4,911,920 | 3/1990 | Jani et al. . |
| 5,106,615 | 4/1992 | Dikstein ............ 424/78.04 |
| 5,192,535 | 3/1993 | Davis et al. ............ 424/78.04 |

FOREIGN PATENT DOCUMENTS

| | | |
|---|---|---|
| 0028110 | 5/1981 | European Pat. Off. . |
| 63-43930 | 2/1988 | Japan ................... 522/153 |
| 2007091 | 5/1979 | United Kingdom . |
| 2013084 | 8/1979 | United Kingdom . |
| WO89/06964 | 8/1989 | WIPO . |

OTHER PUBLICATIONS

N. Unlu et al; "Formulation of Carbopol 940 Opthalmic Vehicles, and in vitro evaluation of the Influence of Simulated Lacrimal Fluid on their Physico-Chemical Properties"; Die Pharmazie; vol. 46; No. 11, Nov. 1991; pp. 784–788.

Derwent Publications Ltd.; Database WPIL; & JP-A-60-235815; (Sansui Denki KK); Nov. 1985 Abstract.

United States Pharmacopoeia, "Carbomer 910", issued 1989, p. 1910.

Japanese Standards of Pharmaceutical Ingredients 1991 Part II, "Carboxyvinyul Polymer", pp. 1177–1180.

Primary Examiner—G. S. Kishore
Assistant Examiner—Peter F. Kulkosky
Attorney, Agent, or Firm—Frishauf, Holtz, Goodman & Woodward

[57] ABSTRACT

A carboxyvinyl polymer having Newtonian viscosity, ophthalmic preparations containing the polymer, a process for preparing the polymer, and a vehicle for ophthalmic preparations containing the polymer. By using the polymer in a vehicle, an ophthalmic preparation having a low viscosity and a desirable permeability of a drug can be obtained.

20 Claims, 2 Drawing Sheets

CARBOXYVINYL POLYMER HAVING NEWTONIAN VISCOSITY

FIELD OF THE INVENTION

This invention relates to a novel carboxyvinyl polymer having Newtonian viscosity, a process for preparing the same and ophthalmic preparations containing the same.

DESCRIPTION OF THE PRIOR ART

A carboxyvinyl polymer is a water soluble copolymer of acrylic acid partially crosslinked by various crosslinking agents such as polyallylsucrose. Various carboxyvinyl polymers having molecular weights ranging from one million to three millions and various viscosities have been applied in cosmetics, pharmaceutics, chemical engineering and other fields. Examples of such carboxyvinyl polymers are Carbomer 910 in the United States Pharmacopoeia, of which a 1% (W/V) aqueous solution has such a low viscosity ranging from 3000 to 7000 centipoises (hereinafter referred to as cP), and carboxyvinyl polymer in the Japanese Standards of Pharmaceutical Ingredients, of which a 0.2% (W/V) aqueous solution has such a high viscosity ranging from 1500 to 50000 cP.

It is a feature of these carboxyvinyl polymers to have non-Newtonian viscosity having a high yield value. Namely, the utility of the carboxyvinyl polymer is that a very high viscosity can be obtained by adding a small amount thereof. Yield value means a value of shear stress when the shear rate is zero in the case where the viscosity of a solution is measured by a rotating viscometer.

In an ophthalmic application, carboxyvinyl polymers contained in an ophthalmic preparation as a vehicle for sustained release of a drug have been known (Japanese Unexamined Patent Publications 67021/1979, 110312/1979, 503201/1990). These prior arts disclosed that sustained release of a drug can be achieved by keeping a drug dissolved in an aqueous solution containing a carboxyvinyl polymer, which becomes a gel, on the cornea for a long period with the help of the high viscosity of the carboxyvinyl polymer and by gradual degradation of the gel. Therefore, the carboxyvinyl polymers of the above-described prior arts are limited to those having a viscosity of 1000 cP or more and they teach that such a high viscosity is necessary for sustained release effect of a drug.

As mentioned above, the feature of the prior arts is to utilize the property of the carboxyvinyl polymer having non-Newtonian viscosity, the property being that the polymer provides high viscosity to ophthalmic preparations by addition of the same even in a small amount.

Application of a conventional carboxyvinyl polymer having non-Newtonian viscosity to ophthalmic preparations has an advantage of sustained release, and, on the other hand, a disadvantage of excessively high viscosity. Since a foreign body sensation occurs when the viscosity of an ophthalmic preparation is high, it is desirable that viscosity of an ophthalmic preparation is as low as possible. Especially, when the viscosity is 10000 cP or more, the ophthalmic preparation becomes like an eye ointment, with the result that it is difficult for a patient to instill such ophthalmic preparation in a constant volume from an eyedropper, and further, it is even difficult to instill the ophthalmic preparation by himself. Consequently, it is necessary for the patient to have the ophthalmic preparation applied to the conjunctival sac by a medical doctor.

Further, various problems exist in the process of preparing a highly viscous ophthalmic preparation having a viscosity of 1000 cP or more. For example, the preparation contains air bubbles which are difficult to remove, and it is impossible to sterilize the preparation by filtration.

It is, therefore, desirable that viscosity of an ophthalmic preparation is less than 1000 cP for convenience of application and in order to avoid the problems in production.

An approach to solve these problems is to extremely reduce the amount of the carboxyvinyl polymer to be added in order to adjust the viscosity to be less than 1000 cP. FIG. 1 shows relationships between concentration and viscosity of known carboxyvinyl polymers. While the problem of viscosity is solved by using this approach, these carboxyvinyl polymers can be added only in such an extremely low concentration, as is clear from FIG. 1, that the expected effect by adding the polymer cannot be exerted.

A carboxyvinyl polymer is expected to exert an effect of enhancing permeability of a drug, which no prior arts have disclosed yet, and study on such as novel effect of a carboxyvinyl polymer is desired. However, with an extremely small amount of carboxyvinyl polymer to be added, such effect cannot be expected. Accordingly, development of a novel carboxyvinyl polymer is desired.

SUMMARY OF THE INVENTION

In view of this, the inventors investigated a carboxyvinyl polymer from which ophthalmic preparations having a low viscosity can be obtained even if the amount of the carboxyvinyl polymer to be added is not extremely reduced. As the result, the inventors found a carboxyvinyl polymer which has a low yield value and Newtonian viscosity. The inventors also found that by using the carboxyvinyl polymer ophthalmic preparations having a viscosity of less than 1000 cP and simultaneously maintaining a sufficient concentration to exert the effect by adding the polymer can be obtained.

First, the inventors studied a process for preparing a carboxyvinyl polymer having Newtonian viscosity and found that the polymer can be prepared by shearing a carboxyvinyl polymer having non-Newtonian viscosity with the use of an ultrasonic generating device and so forth.

Next, the inventors studied the obtained carboxyvinyl polymer having Newtonian viscosity with respect to permeability of a drug by adding the polymer to ophthalmic preparations and found that the polymer enhances permeability of a drug.

This invention relates to a novel carboxyvinyl polymer having Newtonian viscosity (hereinafter referred to as N-CVP), a process for preparing the same and ophthalmic preparations containing the same.

According to a first aspect of the present invention, N-CVP is provided. The yield value of N-CVP is preferably not more than 0.5 dyne/cm$^2$. The relationship between shear stress and shear rate thereof is approximately linear. N-CVP has a molecular weight ranging preferably from 20,000 to 500,000.

According to a second aspect of the present invention, a process for preparing N-CVP is provided. The process comprises shearing carboxyvinyl polymer having non-Newtonian viscosity in an aqueous solution. In this process, the shearing is carried out with an ultrasonic generating device, a high pressure homogenizer, a high speed stirrer, etc.

According to a third aspect of the present invention, ophthalmic preparations and vehicle thereof are provided.

The preparations contain N-CVP in a vehicle. The concentration of N-CVP ranges preferably from 0.1% to 5% (W/V). The viscosity of the preparations is preferably less than 1000 cP.

By using N-CVP obtained in the present invention, an ophthalmic solution having low viscosity and good permeability of a drug can be provided.

DETAILED DESCRIPTION OF THE INVENTION

Figure 1:
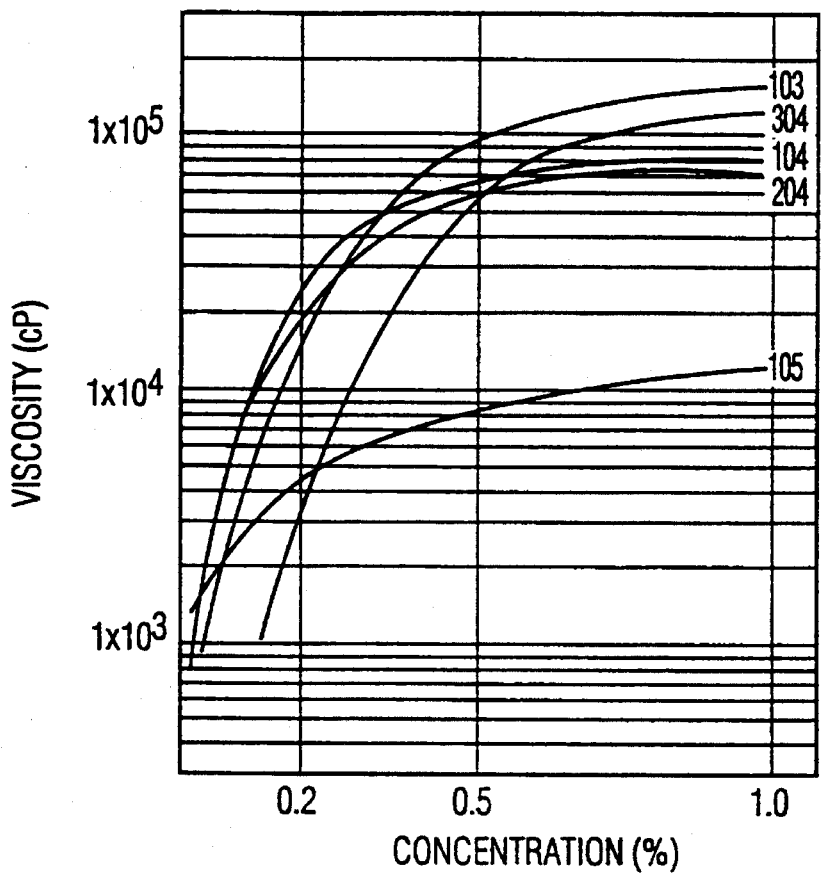
FIG. 1 is a graph showing relationships between concentration and viscosity of various carboxyvinyl polymers commercialized by Wako Pure Chemical Industries Co. The graph is reproduced from Wako's brochure. The ordinate designates viscosity (cP) and the abscissa designates concentration (%).

In the present invention, N-CVP stands for a copolymer of acrylic acid crosslinked by: polyalkenylpolyether such as polyallylsucrose or polyallylpentaerythritol; bifunctional a crosslinking agent such as divinylglycol or divinylbenzene; a non-hydrophilic diolefin crosslinking agent; etc.; and when the viscosity of the aqueous solution of N-CVP is measured by using a rotating viscometer, N-CVP shows a low yield value,. preferably not more than 0.5 dyn/cm$^2$ and almost a linear relationship between the shear stress and the shear rate.

The N-CVP of the present invention is characterized by having a low yield value and almost a linear relationship between the shear stress and the shear rate, and not directly characterized by molecular weight, which can be estimated from the value of intrinsic viscosity. The molecular weight of the N-CVP is estimated to be approximately one-fifth to one-fiftieth of that of known carboxyvinyl polymer having non-Newtonian viscosity used as a raw material, namely within the range of approximately 20,000 to 500,000.

The ophthalmic preparation containing N-CVP can be applied to almost all of the therapeutic fields such as anti-viral, anti-glaucoma, anti-cataract, anti-inflammatory, anti-allergy or diagnosis. The application is not restricted by the nature of the drug substance, accordingly the N-CVP can be applied to various drugs used in ophthalmology as well as a conventional carboxyvinyl polymer having non-Newtonian viscosity.

A process for preparing the N-CVP of the present invention is to change the viscosity of a carboxyvinyl polymer having non-Newtonian viscosity to Newtonian viscosity by shearing the carboxyvinyl polymer in an aqueous solution with the use of an apparatus which has a function of shearing. Examples of the apparatus used are an ultrasonic generating device, a high pressure homogenizer such as Manton Gaulin or a microfluidizer, or a high speed stirrer. Such carboxyvinyl polymers having non-Newtonian viscosity are commercialized under the trade names of Carbopol 910, 934, 934P, 940, 941, 976 by Goodrich Chemical Co., and also Hiviswako 103, 104, 105, 204, 304 by Wako Pure Chemical Industries Co.

As will be described in detail in the article of the measurement of viscosity, while a carboxyvinyl polymer having non-Newtonian viscosity showed a high yield value, which is a feature thereof, N-CVP showed a low yield value and the viscosity of the solution of the N-CVP is much lower than that of the carboxyvinyl polymer having non-Newtonian viscosity.

An ophthalmic preparation in which N-CVP is applied contains few air bubbles and can be sterilized by filtration, whereas ophthalmic preparations containing conventional carboxyvinyl polymer cannot be sterilized. Therefore, the ophthalmic preparation containing N-CVP is prepared much more easily than that containing conventionally known carboxyvinyl polymer.

Since the viscosity of the ophthalmic preparation containing the N-CVP is low, there exists the merits that it is possible for a patient to instill the ophthalmic preparation by himself and it is also possible to instill the ophthalmic preparation in a constant volume from an eyedropper.

To examine the effect of N-CVP, the inventors tested the permeability of a drug by instilling the ophthalmic preparation of the present invention containing N-CVP, and a preparation which does not contain N-CVP as a control, respectively to rabbit eyes. As will be described in detail detailing the article of permeability test, the area under the curve, which shows the concentration of a drug in tissues, of the ophthalmic preparation of the present invention was obviously larger than that of the control, leading to the conclusion that the N-CVP of the present invention greatly enhances the permeability of a drug.

In other words, N-CVP can increase a drug concentration in tissues by enhancing the permeability of a drug, thereby improving the permeabilty of a drug which is hardly absorbed in tissues, and decreasing a dosage and administration frequency.

The ophthalmic preparation of the present invention can be prepared by known methods using N-CVP. For example, a drug and N-CVP are added to sterile purified water, and finally the pH of the mixture is adjusted by using a pH adjusting agent such as sodium chloride or dilute hydrochloric acid, thereby giving the preparation. If necessary, a tonicity agent such as sodium chloride, potassium chloride or glycerin, a buffering agent such as sodium phosphate or potassium phosphate, a stabilizer such as disodium edetate, a preservative such as ethyl p-hydroxybenzoate, butyl p-hydroxybenzoate or sorbic acid, etc. can be added to the preparation.

The ophthalmic preparation of the present invention can also be prepared by shearing the solution of carboxyvinyl polymer having non-Newtonian viscosity, and then adding some kinds of additive without isolating the resulting N-CVP.

The pH range of the ophthalmic preparation of the present invention can be varied within a range applicable to ophthalmic preparations conventionally used. The preferable range is 3 to 8. The amount of N-CVP to be added is determined to be such that the viscosity of the ophthalmic preparation is less than 1000 cP, which slightly varies according to pH or the preparation process. The preferable concentration is 0.1 to 5% (W/V). The more preferable range is 0.1 to 2% (W/V).

Examples of preparation of the N-CVP and ophthalmic preparations thereof are shown below.

1. Preparation of N-CVP

EXAMPLE 1

Hiviswako 105 (1.0 g, Wako Pure Chemical Industries Co.) was dissolved in water (100 ml). The solution was treated for 9 minutes with a probe type ultrasonic generating device (oscillating frequency: 20 kHz) and the solution was lyophilized to give N-CVP (quantitative).

By the same method as described above with the exception that the treating time was varied, N-CVP having various yield values was obtained from commercialized carboxyvinyl polymers.

EXAMPLE 2

Carbopol 976 (1.0 g, Goodrich Chemical Co.) was dissolved in water (100 ml). The solution was stirred for 30 minutes with a high speed stirrer (10000 revolutions per minute) and the solution was lyophilized to give N-CVP (quantitative).

By the same method as described above with the exception that the stirring time was varied, N-CVP having various yield values was obtained from commercialized carboxyvinyl polymers.

2. Measurement of Viscosity

To examine the nature of N-CVP obtained in Example 1, a 0.2% (W/V) aqueous solution of N-CVP was adjusted to pH 7 and the viscosity of the solution was measured with a rotating viscometer (Rotovisco CV20 type viscosity meter: HAAKE Co.) at 25° C. For comparison, an aqueous solution of Hiviswako 105 (Wako Pure Chemical Industries Co.), as a typical example of conventional carboxyvinyl polymer, was prepared and the viscosity was measured in the same manner as the above.

Figure 2:
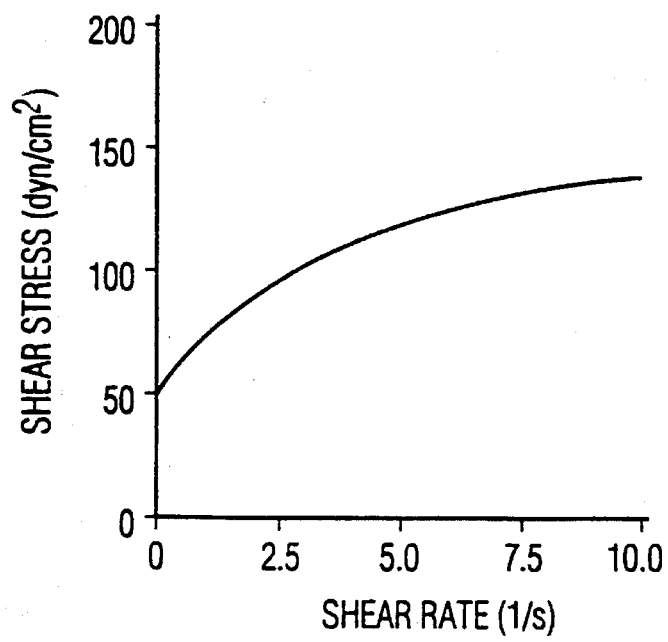
FIG. 2 is a graph showing the relationship between the shear stress and the shear rate of a 0.2% aqueous solution of Hiviswako 105 (pH 7.0) measured with a rotating viscometer. The ordinate designates shear stress (dyn/cm$^2$) and the abscissa designates shear rate (l/s).

As shown in FIG. 2, Hiviswako 105 has a high yield value (yield value means the shear stress when the shear rate is 0) of 52 dyn/cm$^2$ and shows non-Newtonian viscosity, which is represented by a nonlinear relationship between the shear stress and the shear rate.

Figure 3:
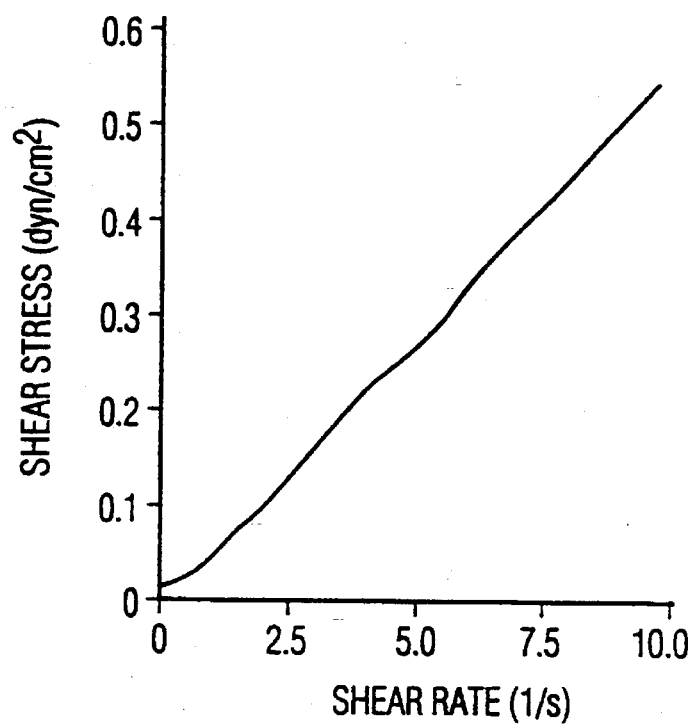
FIG. 3 is a graph showing the relationship between the shear stress and the shear rate of a 0.2 % aqueous solution of N-CVP (pH 7.0) obtained in Example 1, measured with a rotating viscometer. The ordinate designates shear stress (dyn/cm$^2$) and the abscissa designates shear rate (l/s).

As shown in FIG. 3, the N-CVP obtained in Example 1 shows a low yield value of 0.02 dyn/cm$^2$ and a linear relationship between the shear stress and the shear rate, thereby indicating that the N-CVP has Newtonian viscosity. The N-CVP of Example 1 also shows such an extremely low viscosity as 6 cP at a shear rate of 1.92 (l/second), as compared with Hiviswako 105 which shows a viscosity of 4700 cP.

As shown above, when N-CVP is used instead of a carboxyvinyl polymer having non-Newtonian viscosity, the high yield value, which is a feature of a carboxyvinyl polymer having non-Newtonian viscosity, turns into a low yield value and the viscosity of the solution is greatly lowered.

3. Measurement of Molecular Weight

The relationship between intrinsic viscosity ([η]) and molecular weight (M) is represented by the following formula (1):

$$[\eta] = KM^{\alpha} \qquad (1)$$

wherein K and α stand for empirical constants respectively.

The molecular weight of N-CVP is calculated by using the above formula.

The N-CVP obtained in Example 1 was dissolved in a 0.9% aqueous solution of sodium chloride to give a concentration of 0.08% (W/V).

Then, the viscosity ($\eta_1$) of the solution was measured with a Ubbelohde type viscometer. The viscosity ($\eta_2$) of a 0.9% sodium chloride aqueous solution, which was the solvent, was also measured in the same manner. By using these values measured, specific viscosity, which is represented by the following formula, was calculated.

$$\eta_3 = (\eta_1/\eta_2) - 1$$

Then, intrinsic viscosity, which equals reduced viscosity obtained by dividing the specific viscosity by concentration of solute, was obtained. For comparison, Hiviswako 105 was treated in the same manner as above and the intrinsic viscosity thereof was obtained.

The molecular weight of N-CVP which was calculated by using the intrinsic viscosity and the constants obtained with reference to dextran ( K=9.00×10$^{-4}$, α=0.50, described in KOBUNSHIKAGAKU (high-molecular chemistry), 13, 20, (1956)) was 118,000 and that of Hiviswako 105 was 1,600,000.

These results show that the molecular weight of N-CVP obtained by shearing according to the manner of Example 1 is approximately one-fourteenth of that of Hiviswako.

4. Preparation of Ophthalmic Preparation

Preparing Example 1

| Formulation 1-1 | |
| --- | --- |
| Carbopol 976 (Goodrich Chemical Co.) | 1.3 g |
| Fluorescein sodium salt | 0.01 g |
| Sodium chloride | 0.9 g |
| Sodium hydroxide | q.s. |
| Sterile purified water | q.s. |
| Total | 100 ml |

Process for preparation: Carbopol 976 was dissolved in sterile purified water and the solution was adjusted to pH 4.3 with sodium hydroxide, then treated for 5 minutes with a probe type ultrasonic generating device (oscillating frequency: 20 kHz) to give a solution having Newtonian viscosity. Then, fluorescein sodium salt and sodium chloride were added to the solution. The viscosity of the solution was measured at 25 ° C. at a shear rate of 1.92 (l/second) by using a Rotovisco CV 20 viscometer (Haake Co.) with the result that the viscosity was 260 cP. Hereinafter, viscosities were measured under the same conditions.

Ophthalmic preparations having the following formulations can be obtained in the same manner as Formulation 1—1.

| Formulation 1-2 (viscosity: 20 cP) | |
|---|---|
| Carbopol 976 (Goodrich Chemical Co.) | 0.1 g |
| Fluorescein sodium salt | 0.01 g |
| Sodium chloride | 0.9 g |
| Sodium hydroxide | q.s. |
| Sterile purified water | q.s. |
| Total | 100 ml |

| Formulation 1-3 (viscosity: 400 cP) | |
|---|---|
| Carbopol 976 (Goodrich Chemical Co.) | 2.0 g |
| Fluorescein sodium salt | 0.01 g |
| Sodium chloride | 0.9 g |
| Sodium hydroxide | q.s. |
| Sterile purified water | q.s. |
| Total | 100 ml |

Preparing Example 2

| Formulation 2-1 (viscosity: 500 cP) | |
|---|---|
| Hiviswako 105 (Wako Pure Chemical Industries Co.) | 1.5 g |
| Betamethasone phosphate | 0.1 g |
| Sodium chloride | 0.9 g |
| Ethyl p-oxybenzoate | 0.008 g |
| Butyl p-oxybenzoate | 0.004 g |
| Sodium hydroxide | q.s. |
| Sterile purified water | q.s. |
| Total | 100 ml |

Process for preparation: Hiviswako 105 was dissolved in sterile purified water and the solution was stirred for 10 minutes with a high speed stirrer (10,000 revolutions per minute). Betamethasone phosphate, sodium chloride, ethyl p-oxybenzoate and butyl p-oxybenzoate were added to the solution, and then pH of the solution was adjusted to 6.0 by adding sodium hydroxide.

Preparing Example 3

| Formulation 3-1 (viscosity: 15 cP) | |
|---|---|
| N-CVP | 1.0 g |
| Pirenoxine | 0.005 g |
| Sodium chloride | 0.9 g |
| Ethyl p-oxybenzoate | 0.008 g |
| Butyl p-oxybenzoate | 0.004 g |
| Sodium hydroxide | q.s. |
| Sterile purified water | q.s. |
| Total | 100 ml |

Process for preparation: N-CVP obtained in Example 1 was dissolved in sterile purified water. Then, Pirenoxine, sodium chloride, ethyl p-oxybenzoate and butyl p-oxybenzoate were added to the solution. After that, the pH of the solution was adjusted to 6.0 by adding sodium hydroxide.

By using the same method as in Preparing Example 3, an ophthalmic preparation having the following formulation was obtained.

| Formulation 3-2 (viscosity: 5 cP) | |
|---|---|
| N-CVP | 0.2 g |
| Pilocarpine hydrochloride | 1.0 g |
| Sodium chloride | 0.6 g |
| Sorbic acid | 0.1 g |
| Sodium hydrogen phosphate | q.s. |
| Sodium hydroxide | q.s. |
| Sterile purified water | q.s. |
| Total | 100 ml |

Permeability Test

To examine the effect of N-CVP, the permeability of a drug was investigated by instilling an ophthalmic preparation of the invention to rabbits.

The ophthalmic prepartion of the formulation 1—1, which is a typical example of this invention, was instilled to rabbit eyes ( 1 group 5 rabbits) and the concentration of fluorescein in aqueous humor was measured after 1, 2, 3, 4, 6 and 8 hours with a fluorescence spectrophotometer. As the control, an ophthalmic preparation similar to the formulation 1—1 except that carboxyvinyl polymer was not contained was used.

Figure 4:
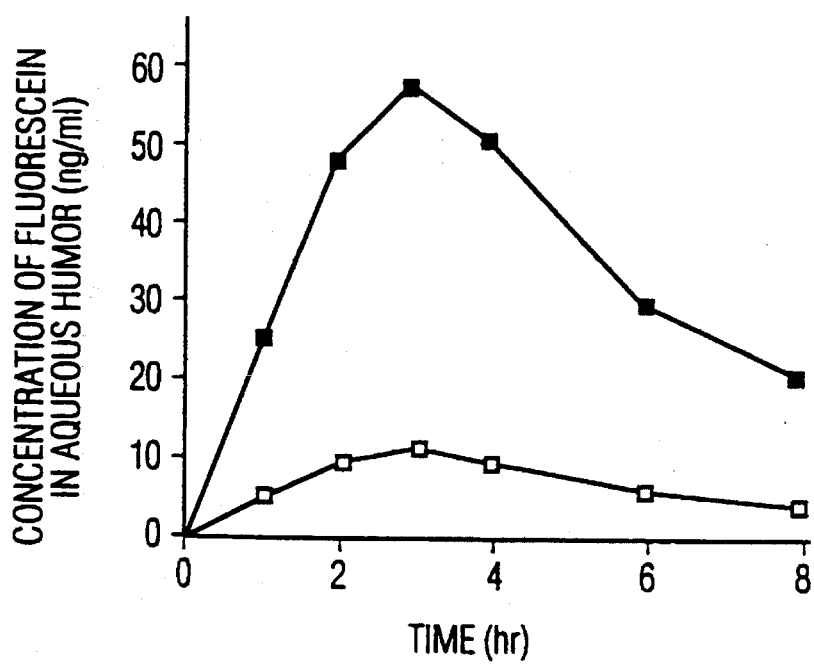
FIG. 4 is a graph showing the concentration of fluorescein in an aqueous humor of rabbit eyes measured at each measuring time after a preparation of the present invention and a control both containing fluorescein, were respectively instilled to rabbit eyes. The ordinate designates concentration (ng/ml) and the abscissa designates time (hr). —■— designates the concentration obtained with the preparation of the present invention and —□— designates that obtained with the control.

The concentration of fluorescein in the aqueous humor at each measuring time is shown in FIG. 4. The area under the curve (AUC), which was calculated from the measured value, is shown in Table 1.

TABLE 1

| | AUC (ng · hr/ml) | |
|---|---|---|
| Ophthalmic preparation of the present invention (Formulation 1-1) | 282.9 | 47.6 |
| Control | 54.4 | 5.2 |

As shown in FIG. 4 and Table 1, the permeability of the ophthalmic preparation which contains N-CVP is 5 times better than that of the control, which does not contain N-CVP.

This result proves that the N-CVP of the present invention enhances drug permeability.

What we claim is:

1. An isolated, water soluble carboxyvinyl polymer having a molecular weight of 20,000 to 500,000 as determined by intrinsic viscosity, said polymer when dissolved in water forming an aqueous solution having Newtonian viscosity and having a viscosity of less than 1000 centipoises, said isolated carboxyvinyl polymer being derived by ultrasonic or mechanical shearing of an aqueous solution of a partially crosslinked acrylic acid polymer.

2. The carboxyvinyl polymer as defined in claim 1 wherein said carboxyvinyl polymer has a yield value which is not more than 0.5 dyne/cm$^2$.

3. The carboxyvinyl polymer as defined in claim 2 wherein said carboxyvinyl polymer exhibits an approximately linear relationship between shear stress and shear rate.

4. A process for preparing a carboxyvinyl polymer as defined in claim 1 wherein the shearing is carried out with an ultrasonic generating device.

5. The process for preparing a carboxyvinyl polymer as defined in claim 1 wherein the shearing is carried out with a high pressure homogenizer.

6. The process for preparing a carboxyvinyl polymer as defined in claim 1 wherein the shearing is carried out with a high speed stirrer.

7. A vehicle for ophthalmic preparations comprising a carboxyvinyl polymer having Newtonian viscosity as defined in claim 1 and a pharmaceutically acceptable carrier.

8. The vehicle for ophthalmic preparations as defined in claim 7 wherein the concentration of said carboxyvinyl polymer having Newtonian viscosity is from 0.1% to 5% (W/V).

9. An ophthalmic preparation which comprises a carboxyvinyl polymer having Newtonian viscosity as defined in claim 1 and a drug, wherein the carboxyvinyl polymer has a drug permeability enhancing effect.

10. The ophthalmic preparation as defined in claim 9 wherein the concentration of said carboxyvinyl polymer having Newtonian viscosity is from 0.1 to 5% (W/V).

11. The carboxyvinyl polymer as defined in claim 2 wherein the yield value is 0.02 dyn/cm$^2$ and the viscosity is 6 cP at a shear rate of 1.92 l/seconds.

12. The carboxyvinyl polymer as defined in claim 1 wherein the molecular weight is 118,000.

13. The vehicle for ophthalmic preparations as defined in claim 7 wherein said carboxyvinyl polymer is in a concentration of 0.1 to 2% (W/V); said preparation has a pH of 3 to 8; and said carboxyvinyl polymer has a yield value of not more than 0.5 dyn/cm$^2$.

14. The vehicle as defined in claim 7 wherein the vehicle is in the form of an aqueous solution.

15. The vehicle as defined in claim 8 wherein the vehicle is in the form of an aqueous solution.

16. A method for enhancing the adsorption of a medicament in a preparation comprising adding to said preparation an effective adsorption enhancing amount of a carboxyvinyl polymer having Newtonian viscosity as defined in claim 1.

17. The method as defined in claim 16 wherein said carboxyvinyl polymer has a yield value of not more than 0.5 dyn/cm$^2$, and exhibits an approximately linear relationship between shear stress and shear rate.

18. The carboxyvinyl polymer as defined in claim 1, wherein the crosslinking agent is selected from the group consisting of a polyalkenylpolyether, divinylglycol, divinylbenzene and a non-hydrophilic diolefin.

19. The carboxyvinyl polymer as defined in claim 1, wherein the crosslinking agent is selected from the group consisting of polyallylsucrose and polyallylpentaerythritol.

20. An aqueous solution of a carboxyvinyl polymer, the carboxyvinyl polymer having a molecular weight of 20,000 to 500,000 as determined by intrinsic viscosity, the carboxyvinyl polymer being produced by partially crosslinking acrylic acid with an organic crosslinking agent having one or more unsaturated bonds, the solution being subjected to ultrasonic or mechanical shearing wherein the polymer solution has Newtonian viscosity and has a viscosity of less than 1000 centipoises.

* * * * *